(12) United States Patent
Mitsui

(10) Patent No.: US 12,241,055 B2
(45) Date of Patent: Mar. 4, 2025

(54) BACTERIUM DEGRADING MICROORGANISM, MICROBIAL PREPARATION, AND METHOD AND DEVICE FOR DEGRADING MICROORGANISM

(71) Applicants: SUMITOMO CHEMICAL COMPANY, LIMITED, Tokyo (JP); KATAOKA BIO LABORATORY CO., LTD., Isehara (JP)

(72) Inventor: Tomokazu Mitsui, Osaka (JP)

(73) Assignees: SUMITOMO CHEMICAL COMPANY, LIMITED, Tokyo (JP); KATAOKA BIO LABORATORY CO., LTD., Isehara (JP)

( * ) Notice: Subject to any disclaimer, the term of this patent is extended or adjusted under 35 U.S.C. 154(b) by 829 days.

(21) Appl. No.: 17/280,710

(22) PCT Filed: Sep. 27, 2019

(86) PCT No.: PCT/JP2019/038437
§ 371 (c)(1),
(2) Date: Mar. 26, 2021

(87) PCT Pub. No.: WO2020/067555
PCT Pub. Date: Apr. 2, 2020

(65) Prior Publication Data
US 2021/0380932 A1   Dec. 9, 2021

(30) Foreign Application Priority Data

Sep. 28, 2018   (JP) .................................. 2018-185192

(51) Int. Cl.
C12N 1/20      (2006.01)
C02F 11/02     (2006.01)
C12R 1/01      (2006.01)

(52) U.S. Cl.
CPC .............. *C12N 1/205* (2021.05); *C02F 11/02* (2013.01); *C02F 2303/04* (2013.01); *C12R 2001/01* (2021.05)

(58) Field of Classification Search
CPC ...... C12N 1/205; C02F 11/02; C02F 2303/04; C12R 2001/01
See application file for complete search history.

(56) References Cited

U.S. PATENT DOCUMENTS 4,818,817 A   4/1989   Shoham et al.

FOREIGN PATENT DOCUMENTS

| JP | 2003-62599 A | 3/2003 |
| KR | 10-2013-0056585 A | 5/2013 |
| WO | WO 03/072014 A2 | 9/2003 |

OTHER PUBLICATIONS

Wang et al (World Journal of Microbiology & Biotechnology 19: 427-432, 2003) (Year: 2003).*
Janda et al (J Clin Microbiol. Sep. 2007;45(9):2761-4) (Year: 2007).*
Bowman et al (PLoS One. Aug. 18, 2015; 10(8):e0135868) (Year: 2015).*
"Fiscal year of Heisei 27, Report on current status of industrial waste treatment, Results of Heisei 25 (Digest edition)" Minister's Secretariat, Ministry of the Environment Waste Management and Recycling Department, Mar. 2016, 148 pages.
International Search Report (PCT/ISA/210) issued in PCT/JP2019/038437, dated Oct. 29, 2019.
Steven et al., "*Tumebacillus permanentifrigoris* gen. nov., sp. nov., an aerobic, spore-forming bacterium isolated from Canadian high Arctic permafrost," International Journal of Systematic and Evolutionary Microbiology, vol. 58, 2008, pp. 1497-1501.
Wang et al., "*Tumebacillus flagellatus* sp. nov., an α-amylase/pullulanase-producing bacterium isolated from cassava wastewater," International Journal of Systematic and Evolutionary Microbiology, vol. 63, 2013, pp. 3138-3142.
Yamamoto, "Combustion Technology of the Sewage Sludge," Journal of the Combustion Society of Japan, vol. 53, No. 164, 2011, pp. 91-96.
Indonesian Office Action for Indonesian Application No. P00202102975, dated Nov. 9, 2022, with an English translation.
Chinese Office Action and Search Report for Chinese Application No. 201980063877.6, dated Dec. 11, 2023, with English translation.
"*Tumebacillus* sp. 7B-408 16S ribosomal RNA gene, partial sequence," Database GenBank [online], Accession No. KF441681, uploaded on Jul. 17, 2014, retrieved on Jul. 10, 2023, URL: <https://www.ncbi.nlm.nih.gov/nuccore/542215135?sat=4&satkey=116434385>.
Japanese Office Action for Japanese Application No. 2020-549508, dated Jul. 18, 2023, with an English translation.
Japanese Office Action for corresponding Japanese Application No. 2020-549508, dated Oct. 24, 2023, with English translation.
Sun et al., "Assessing the Relative Effects of Geographic Location and Soil Type on Microbial Communities Associated with Straw Decomposition," Applied and Environmental Microbiology, vol. 79, No. 11, 2013, pp. 3327-3335.
Taiwanese Office Action and Search Report for Taiwanese Application No. 108135333, dated Oct. 13, 2023, with an English translation.

(Continued)

*Primary Examiner* — Thomas J. Visone
*Assistant Examiner* — Georgiana C Reglas
(74) *Attorney, Agent, or Firm* — Birch, Stewart, Kolasch & Birch, LLP

(57) ABSTRACT

Provided are a bacterium having a 16S rRNA gene comprising a nucleotide sequence having 98.2% or more identity to the nucleotide sequence represented by SEQ ID NO: 1, and having an ability to degrade a target microorganism, a microbial preparation for degrading a target microorganism, comprising a bacterium (a1), and a method for degrading a target microorganism and a device for degrading a target microorganism using the same. Bacterium (a1) is a bacterium having a 16S rRNA gene comprising a nucleotide sequence having 90% or more identity to the nucleotide sequence represented by SEQ ID NO: 1, and having an ability to degrade a target microorganism.

2 Claims, 1 Drawing Sheet

Specification includes a Sequence Listing.

(56) References Cited

OTHER PUBLICATIONS

Kim, "Evaluation on applicability of microbial products for reservoirs and wastewater treatment," Department of Environmental Engineering, University of Seoul, 2012, 94 pages total, with an English abstract.
Korean Office Action for Korean Application No. 10-2021-7011805, dated Sep. 26, 2024, with an English translation.
Wu et al., "Tumebacillus algifaecis sp. nov., isolated from decomposing algal scum," International Journal of Systematic and Evolutionary Microbiology, vol. 65, 2015, pp. 2194-2198 (7 pages total).

* cited by examiner

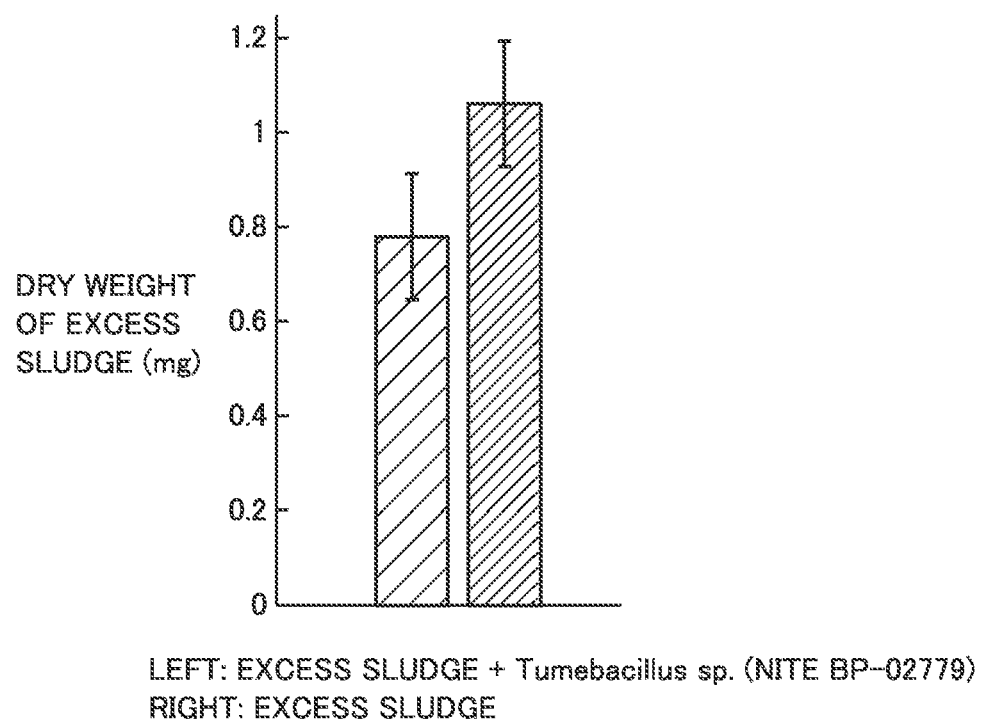

SEQUENCE LISTING

```
<160> NUMBER OF SEQ ID NOS: 16

<210> SEQ ID NO 1
<211> LENGTH: 1471
<212> TYPE: DNA
<213> ORGANISM: Tumebacillus sp. NITE BP-02779

<400> SEQUENCE: 1
acgaacgctg gcggcgtgcc taatacatgc aagtcgagcg gagtgtmgag agcttgctct      60
cwraggtcag cggcggacgg gtgagtaaca cgtgggtaac ctgcctggca gactgggata     120
acgcttggaa acgagtgcta ataccggata atctcttgga tcgcatggtc tgagagtaaa     180
aggagctttt gcttcactgc yagatggacc cgcggcgcat tagctagttg gtgaggtaat     240
ggctcaccaa ggcgacgatg cgtagccgac ctgagagggt gaccggccac actgggactg     300
agacacggcc cagactccta cgggaggcag cagtagggaa tcttccgcaa tgggcgcaag     360
cctgacggag caacgccgcg tgagtgatga aggccttcgg gttgtaaaac tctgtcttct     420
gtgaagaacc atcctgtgca gagaaagctc aggacctgac ggtaacagag gaggaagccc     480
cggctaacta cgtgccagca gccgcggtaa tacgtagggg gcaagcgttg tccggaatca     540
ctgggcgtaa agcgcgcgca ggcggtctct cacgtccggg gtgaaagccc agagctcaac     600
tctgggattg ccttggatac ggggagactt gaggatcgga gaggcaaggg gaattccacg     660
tgtagcggtg aaatgcgtag agatgtggag gaacaccgt ggcgaaggcg ccttgctggc     720
cgatttctga cgctgaggcg cgaaagcgtg gggagcaaac aggattagat accctggtag     780
tccacgccgt aaacgatgag tgctaggtgt taggggggccc accccttagt gccgaagcta     840
acgcattaag cactccgcct ggggagtacg gtcgcaagac tgaaactcaa aggaattgac     900
gggggcccgc acaagcagtg gagcatgtgg tttaattcga agcaacgcga agaaccttac     960
caagacttga catcccgctg accrctctag agatagagyt tcccttcggg gcagcggtga    1020
caggtggtgc atggttgtcg tcagctcgtg tcgtgagatg ttgggttaag tcccgcaacg    1080
agcgcaaccc ctatgttgtg ttgctaccat ttagttgagc acttacaaca gactgccggt    1140
gacaaaccgg aggaaggcgg ggatgacgtc aaatcatcat gccccttatg tcttgggcta    1200
cacacgtgct acaatggacg gtacaaaggg ttgcgaagcc gcgaggtgaa gccaatccca    1260
gaaagccgtt cgtagttcgg attgcaggct gcaactcgcc tgcatgaagc cggaattgct    1320
agtaatcgcg gatcagcatg ccgcggtgaa ttcgttcccg ggccttgtac acaccgcccg    1380
tcacaccatg ggagttggta acacccgaag tcggtgaggt aactgcttgc agagccagcc    1440
gcctaaggtg ggatcgataa ctggggtgaa g                                   1471

<210> SEQ ID NO 2
<211> LENGTH: 20
<212> TYPE: DNA
<213> ORGANISM: Artificial Sequence
<220> FEATURE:
<223> OTHER INFORMATION: synthetic
```

<400> SEQUENCE: 2
agrgtttgat cmtggctcag                                               20

<210> SEQ ID NO 3
<211> LENGTH: 19
<212> TYPE: DNA
<213> ORGANISM: Artificial Sequence
<220> FEATURE:
<223> OTHER INFORMATION: synthetic

<400> SEQUENCE: 3
ggytaccttg ttacgactt                                                19

<210> SEQ ID NO 4
<211> LENGTH: 19
<212> TYPE: DNA
<213> ORGANISM: Artificial Sequence
<220> FEATURE:
<223> OTHER INFORMATION: synthetic

<400> SEQUENCE: 4
ctcctacggg aggcagcag                                                19

<210> SEQ ID NO 5
<211> LENGTH: 18
<212> TYPE: DNA
<213> ORGANISM: Artificial Sequence
<220> FEATURE:
<223> OTHER INFORMATION: synthetic

<400> SEQUENCE: 5
gtattaccgc ggctgctg                                                 18

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
aaactyaaag gaattgacgg                                               20

<210> SEQ ID NO 7
<211> LENGTH: 1470
<212> TYPE: DNA
<213> ORGANISM: Tumebacillus algifaecis NBRC108765t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (172)..(173)
<223> OTHER INFORMATION: n is a, c, g, or t
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature

```
<222> LOCATION: (1427)..(1427)
<223> OTHER INFORMATION: n is a, c, g, or t

<400> SEQUENCE: 7
gacgaacgct ggcggcgtgc ctaatacatg caagtcgagc ggacnggagg gagcttgctc      60
ccaaaggtta gcggcggacg ggtgagtaac acgtgggcaa tctgcccgac agactgggat     120
aacgcttgga aacgagtgct aataccggat aagcgattnc ntcgcatgag gnnatcgaga    180
aagaagcttt cgcttcactg tcggatgagc ccgcggcgca ttagctagtt ggtgaggtaa    240
cggctcacca aggcgacgat gcgtagccga cctgagaggg tgatcggcca cactgggact    300
gagacacggc ccagactcct acgggaggca gcagtaggga atcttccaca atgggcgcaa    360
gcctgatgga gcaacgccgc gtgaatgatg aaggccttcg ggttgtaaaa ttctgtcttc    420
tgtgaagaac aagtgtgaga agngaatgct cacaccctga cggtaacaga ggaggaagcc    480
ccggctaact acgtgccagc agccgcggta atacgtaggg ggcaagcgtt gtccggaatc    540
actgggcgta aagcgcgcgc aggcggccat ctgcgtccgg ggtgaaagcc caaggctcaa    600
ccttgggact gccttggata cgggatggct tgaggatcgg agaggcaagg ggaattccac    660
gtgtagcggt gaaatgcgta gagatgtgga ggaacacctg tggcgaaggc gccttgctgg    720
ccgatttctg acgctgaggc gcgaaagcgt ggggagcaaa caggattaga taccctggta    780
gtccacgccg taaacgatga gtgctaggtg ttgggggggta ccaccctcag tgccgaagct    840
aacgcattaa gcactccgcc tggggagtac ggtcgcaaga ctgaaactca aggaattga    900 cgggggcccg cacaagcagt ggagcatgtg gtttaattcg aagcaacgcg aagaacctta    960
ccaagacttg acatcccgct gaccggttta gagatagacc ttcccttcgg ggcagcggtg   1020
acaggtggtg catggttgtc gtcagctcgt gtcgtgagat gttgggttaa gtcccgcaac   1080
gagcgcaacc cctaaattgt gttgccatca ttcagttggg cactcacaat tgactgccgg   1140
tgacaaaccg gaggaaggcg gggatgacgt caaatcatca tgccccttat gtcttgggct   1200
acacacgtgc tacaatgggc ggtacaaagg gttgcgaggc cgcgaggcgg agccaatccc   1260
aaaaagccgc tcacagttcg gattgcaggc tgcaactcgc ctgcatgaag ctggaattgc   1320
tagtaatcgc ggatcagcat gccgcggtga attcgttccc gggccttgta cacaccgccc   1380
gtcacaccat gggagttggc aacacccgaa gccggtgagg taaccgnaag gagccagccg   1440
tctaaggtgg ggtcgatgac tggggtgaag                                    1470

<210> SEQ ID NO 8
<211> LENGTH: 1479
<212> TYPE: DNA
<213> ORGANISM: Paenibacillus polymyxa JCM 2507t
<220> FEATURE:
<221> NAME/KEY: misc_feature
<222> LOCATION: (1004)..(1004)
<223> OTHER INFORMATION: n is a, c, g, or t
<220> FEATURE:
<221> NAME/KEY: misc_feature
<222> LOCATION: (1248)..(1249)
<223> OTHER INFORMATION: n is a, c, g, or t
<220> FEATURE:
<221> NAME/KEY: misc_feature
<222> LOCATION: (1254)..(1255)
<223> OTHER INFORMATION: n is a, c, g, or t

<400> SEQUENCE: 8
gacgaacgct ggcggcgtgc ctaatacatg caagtcgagc ggggttattt agaagcttgc     60
ttctaattaa cctagcggcg gacgggtgag taacacgtag gcaacctgcc cacaagacag    120
```

| | |
|---|---|
| ggataactac cggaaacggt agctaatacc cgatacatcc ttttcctgca tgggagaagg | 180 |
| aggaaaggcg gagcaatctg tcacttgtgg atgggcctgc ggcgcattag ctagttggtg | 240 |
| gggtaaaggc ctaccaaggc gacgatgcgt agccgacctg agagggtgat cggccacact | 300 |
| gggactgaga cacggcccag actcctacgg aggcagcag tagggaatct tccgcaatgg | 360 |
| gcgaaagcct gacggagcaa cgccgcgtga gtgatgaagg ttttcggatc gtaaagctct | 420 |
| gttgccaggg aagaacgtct tgtagagtaa ctgctacaag agtgacggta cctgagaaga | 480 |
| aagcccggc taactacgtg ccagcagccg cggtaatacg tagggggcaa gcgttgtccg | 540 |
| gaattattgg gcgtaaagcg cgcgcaggcg gctctttaag tctggtgttt aatcccgagg | 600 |
| ctcaacttcg ggtcgcactg gaaactgggg agcttgagtg cagaagagga gagtggaatt | 660 |
| ccacgtgtag cggtgaaatg cgtagagatg tggaggaaca ccagtggcga aggcgactct | 720 |
| ctgggctgta actgacgctg aggcgcgaaa gcgtggggag caaacaggat tagatacct | 780 |
| ggtagtccac gccgtaaacg atgaatgcta ggtgttaggg gtttcgatac ccttggtgcc | 840 |
| gaagttaaca cattaagcat tccgcctggg gagtacggtc gcaagactga aactcaaagg | 900 |
| aattgacggg gacccgcaca agcagtggag tatgtggttt aattcgaagc aacgcgaaga | 960 |
| accttaccag gtcttgacat ccctctgacc ggtctagaga tagnccttc cttcgggaca | 1020 |
| gaggagacag gtggtgcatg gttgtcgtca gctcgtgtcg tgagatgttg ggttaagtcc | 1080 |
| cgcaacgagc gcaacccctta tgcttagttg ccagcaggtc aagctgggca ctctaagcag | 1140 |
| actgccggtg acaaaccgga ggaaggtggg gatgacgtca atcatcatg ccccttatga | 1200 |
| cctgggctac acacgtacta caatggccgg tacaacggga agcgaagnng cganntggag | 1260 |
| ccaatcctag aaaagccggt ctcagttcgg attgtaggct gcaactcgcc tacatgaagt | 1320 |
| cggaattgct agtaatcgcg gatcagcatg ccgcggtgaa tacgttcccg ggtcttgtac | 1380 |
| acaccgcccg tcacaccacg agagtttaca cacccgaag tcggtgaggt aaccgcaagg | 1440 |
| agccagccgc cgaaggtggg gtagatgatt ggggtgaag | 1479 |

<210> SEQ ID NO 9
<211> LENGTH: 1475
<212> TYPE: DNA
<213> ORGANISM: Bacillus amyloliquefaciens NBRC3037
<220> FEATURE:
<221> NAME/KEY: misc_feature
<222> LOCATION: (152)..(152)
<223> OTHER INFORMATION: n is a, c, g, or t

<400> SEQUENCE: 9

| | |
|---|---|
| gacgaacgct ggcggcgtgc ctaatacatg caagtcgagc ggacagatgg gagcttgctc | 60 |
| cctgatgtta gcggcggacg ggtgagtaac acgtgggtaa cctgcctgta agactggat | 120 |
| aactccggga aaccggggct aataccggat gnttgtttga accgcatggt tcagacataa | 180 |
| aaggtggctt cggctaccac ttacagatgg acccgcggcg cattagctag ttggtgaggt | 240 |
| aacggctcac caaggcaacg atgcgtagcc gacctgagag ggtgatcggc cacactggga | 300 |
| ctgagacacg gcccagactc ctacgggagg cagcagtagg gaatcttccg caatggacga | 360 |
| aagtctgacg gagcaacgcc gcgtgagtga tgaaggtttt cggatcgtaa agctctgttg | 420 |
| ttagggaaga acaagtgccg ttcaaatagg gcggcacctt gacggtacct aaccagaaag | 480 |
| ccacggctaa ctacgtgcca gcagccgcgg taatacgtag gtggcaagcg ttgtccggaa | 540 |
| ttattgggcg taaagggctc gcaggcggtt tcttaagtct gatgtgaaag ccccggctc | 600 |
| aaccggggag ggtcattgga aactggggaa cttgagtgca gaagaggaga gtggaattcc | 660 |

```
acgtgtagcg gtgaaatgcg tagagatgtg gaggaacacc agtggcgaag gcgactctct    720
ggtctgtaac tgacgctgag gagcgaaagc gtggggagcg aacaggatta gatacctgg     780 tagtccacgc cgtaaacgat gagtgctaag tgttaggggg tttccgcccc ttagtgctgc    840
agctaacgca ttaagcactc cgcctggga gtacggtcgc aagactgaaa ctcaaaggaa     900
ttgacggggg cccgcacaag cggtggagca tgtggtttaa ttcgaagcaa cgcgaagaac    960
cttaccaggt cttgacatcc tctgacaatc ctagagatag gacgtccct tcggggcag     1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct ttatggagcc   1440
agccgccgaa ggtgggacag atgattgggg tgaag                              1475

<210> SEQ ID NO 10
<211> LENGTH: 1475
<212> TYPE: DNA
<213> ORGANISM: Bacillus subtilis IFO 3134

<400> SEQUENCE: 10
gacgaacgct ggcggcgtgc ctaatacatg caagtcgagc ggacagatgg gagcttgctc     60
cctgatgtta gcggcggacg ggtgagtaac acgtgggtaa cctgcctgta agactgggat    120
aactccggga aaccggggct aataccggat gcttgtttga accgcatggt tcaaacataa    180
aaggtggctt cggctaccac ttacagatgg acccgcggcg cattagctag ttggtgaggt    240
aatggctcac caaggcaacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtaccg ttcgaatagg gcggtacctt gacggtacct aaccagaaag    480
ccacggctaa ctacgtgcca gcagccgcgg taatacgtag gtggcaagcg ttgtccggaa    540
ttattgggcg taagggctc gcaggcggtt ccttaagtct gatgtgaaag ccccggctc     600 aaccggggag ggtcattgga aactggggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gatacctgg    780 tagtccacgc cgtaaacgat gagtgctaag tgttaggggg tttccgcccc ttagtgctgc    840
agctaacgca ttaagcactc cgcctggga gtacggtcgc aagactgaaa ctcaaaggaa     900
ttgacggggg cccgcacaag cggtggagca tgtggtttaa ttcgaagcaa cgcgaagaac    960
cttaccaggt cttgacatcc tctgacaatc ctagagatag gacgtccct tcggggcag     1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
```

```
tcccacaaat ctgttctcag ttcggatcgc agtctgcaac tcgactgcgt gaagctggaa      1320
tcgctagtaa tcgcggatca gcatgccgcg gtgaatacgt tcccgggcct tgtacacacc      1380
gcccgtcaca ccacgagagt ttgtaacacc cgaagtcggt gaggtaacct tttaggagcc      1440
agccgccgaa ggtgggacag atgattgggg tgaag                                 1475
```

<210> SEQ ID NO 11
<211> LENGTH: 1475
<212> TYPE: DNA
<213> ORGANISM: Bacillus subtilis IFO 3026

<400> SEQUENCE: 11

```
gacgaacgct ggcggcgtgc ctaatacatg caagtcgagc ggacagatgg gagcttgctc        60
cctgatgtta gcggcggacg ggtgagtaac acgtgggtaa cctgcctgta agactgggat      120
aactccggga aaccggggct aataccggat ggttgtttga accgcatggt tcaaacataa      180
aaggtggctt cggctaccac ttacagatgg acccgcggcg cattagctag ttggtgaggt      240
aacggctcac caaggcaacg atgcgtagcc gacctgagag ggtgatcggc cacactggga      300
ctgagacacg gcccagactc ctacgggagg cagcagtagg gaatcttccg caatggacga      360
aagtctgacg gagcaacgcc gcgtgagtga tgaaggtttt cggatcgtaa agctctgttg      420
ttagggaaga acaagtaccg ttcgaatagg gcggtacctt gacggtacct aaccagaaag      480
ccacggctaa ctacgtgcca gcagccgcgg taatacgtag gtggcaagcg ttgtccggaa      540
ttattgggcg taaagggctc gcaggcggtt tcttaagtct gatgtgaaag ccccgggctc      600
aaccggggag ggtcattgga aactgggaaa cttgagtgca gaagaggaga gtggaattcc      660
acgtgtagcg gtgaaatgcg tagagatgtg gaggaacacc agtggcgaag gcgactctct      720
ggtctgtaac tgacgctgag gagcgaaagc gtggggagcg aacaggatta gataccctgg      780
tagtccacgc cgtaaacgat gagtgctaag tgttaggggg tttccgcccc ttagtgctgc      840
agctaacgca ttaagcactc cgcctgggga gtacggtcgc aagactgaaa ctcaaaggaa      900
ttgacggggg cccgcacaag cggtggagca tgtggtttaa ttcgaagcaa cgcgaagaac      960
cttaccaggt cttgacatcc tctgacaatc ctagagatag gacgtcccct tcggggcag      1020 agtgacaggt ggtgcatggt tgtcgtcagc tcgtgtcgtg agatgttggg ttaagtcccg      1080
caacgagcgc aacccttgat cttagttgcc agcattcagt tgggcactct aaggtgactg      1140
ccggtgacaa accggaggaa ggtggggatg acgtcaaatc atcatgcccc ttatgacctg      1200
ggctacacac gtgctacaat ggacagaaca aagggcagcg aaaccgcgag gttaagccaa      1260
tcccacaaat ctgttctcag ttcggatcgc agtctgcaac tcgactgcgt gaagctggaa      1320
tcgctagtaa tcgcggatca gcatgccgcg gtgaatacgt tcccgggcct tgtacacacc      1380
gcccgtcaca ccacgagagt ttgtaacacc cgaagtcggt gaggtaacct tttaggagcc      1440
agccgccgaa ggtgggacag atgattgggg tgaag                                 1475
```

<210> SEQ ID NO 12
<211> LENGTH: 1475
<212> TYPE: DNA
<213> ORGANISM: Bacillus subtilis IFO 13169
<220> FEATURE:
<221> NAME/KEY: misc_feature
<222> LOCATION: (257)..(257)
<223> OTHER INFORMATION: n is a, c, g, or t

<400> SEQUENCE: 12

```
gacgaacgct ggcggcgtgc ctaatacatg caagtcgagc ggacagatgg gagcttgctc        60
```

```
cctgatgtta gcggcggacg ggtgagtaac acgtgggtaa cctgcctgta agactgggat    120
aactccggga aaccggggct aataccggat ggttgtttga accgcatggt tcaaacataa    180
aaggtggctt cggctaccac ttacagatgg acccgcggcg cattagctag ttggtgaggt    240
aacggctcac caaggcnacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga caagtaccg ttcgataggg gcggtacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag ccccggctc    600 aaccggggag ggtcattgga aactgggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcggggcag   1020 agtgacaggt ggtgcatggt tgtcgtcagc tcgtgtcgtg agatgttggg ttaagtcccg   1080
caacgagcgc aacccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct tttaggagcc   1440
agccgccgaa ggtgggacag atgattgggg tgaag                              1475
```

<210> SEQ ID NO 13
<211> LENGTH: 1478
<212> TYPE: DNA
<213> ORGANISM: Bacillus sphaericus IFO 3341

<400> SEQUENCE: 13

```
gacgaacgct ggcggcgtgc ctaatacatg caagtcgagc gaacagaaaa ggagcttgct     60
cctttgacgt tagcggcgga cgggtgagta acacgtgggc aacctaccct atagtttggg    120
ataactccgg gaaaccgggg ctaataccga ataatctctt ttacttcatg gtgaaagact    180
gaaagacggc atctcgctgt cgctatagga tgggcccgcg gcgcattagc tagttggtga    240
ggtaacggct caccaaggcg acgatgcgta gccgacctga gagggtgatc ggccacactg    300
ggactgagac acggcccaga ctcctacggg aggcagcagt agggaatctt ccacaatggg    360
cgaaagcctg atggagcaac gccgcgtgag tgaagaaggt tttcggatcg taaaactctg    420
ttgtaaggga agaacaagta cagtagtaac tggctgtacc ttgacggtac cttattagaa    480
agccacggct aactacgtgc cagcagccgc ggtaatacgt aggtggcaag cgttgtccgg    540
aattattggg cgtaaagcgc gcgcaggcgg tcctttaagt ctgatgtgaa agcccacggc    600
tcaaccgtgg agggtcattg gaaactgggg gacttgagtg cagaagagga aagtggaatt    660
```

```
ccaagtgtag cggtgaaatg cgtagagatt tggaggaaca ccagtggcga aggcgacttt    720
ctggtctgta actgacgctg aggcgcgaaa gcgtggggag caaacaggat tagatacccct   780
ggtagtccac gccgtaaacg atgagtgcta agtgttaggg ggtttccgcc ccttagtgct    840
gcagctaacg cattaagcac tccgcctggg gagtacggtc gcaagactga aactcaaagg    900
aattgacggg ggcccgcaca agcggtggag catgtggttt aattcgaagc aacgcgaaga    960
accttaccag gtcttgacat cccgttgacc actgtagaga tatagtttcc cttcggggg    1020
caacggtgac aggtggtgca tggttgtcgt cagctcgtgt cgtgagatgt tgggttaagt   1080
cccgcaacga gcgcaaccct tgatcttagt tgccatcatt tagttgggca ctctaaggtg   1140
actgccggtg acaaaccgga ggaaggtggg gatgacgtca atcatcatg ccccttatga    1200
cctgggctac acacgtgcta caatggacga tacaaacggt tgccaactcg cgagagggag   1260
ctaatccgat aaagtcgttc tcagttcgga ttgtaggctg caactcgcct acatgaagcc   1320
ggaatcgcta gtaatcgcgg atcagcatgc cgcggtgaat acgttcccgg gccttgtaca   1380
caccgcccgt cacaccacga gagtttgtaa cacccgaagt cggtgaggta accttttgga   1440
gccagccgcc gaaggtggga tagatgattg gggtgaag                           1478

<210> SEQ ID NO 14
<211> LENGTH: 1477
<212> TYPE: DNA
<213> ORGANISM: Bacillus sphaericus IFO 3528

<400> SEQUENCE: 14
gacgaacgct ggcggcgtgc ctaatacatg caagtcgagc gaacagagaa ggagcttgct     60
ccttcgacgt tagcggcgga cgggtgagta acacgtgggc aacctacctt atagtttggg    120
ataactccgg gaaaccgggg ctaataccga ataatctgtt tcacctcatg gtgaaacact    180
gaaagacggt ttcggctgtc gctataggat gggcccgcgg cgcattagct agttggtgag    240
gtaacggctc accaaggcga cgatgcgtag ccgacctgag agggtgatcg gccacactgg    300
gactgagaca cggcccagac tcctacggga ggcagcagta gggaatcttc cacaatgggc    360
gaaagcctga tggagcaacg ccgcgtgagt gaagaaggat ttcggttcgt aaaactctgt    420
tgtaagggaa gaacaagtac agtagtaact ggctgtacct tgacggtacc ttattagaaa    480
gccacggcta actacgtgcc agcagccgcg gtaatacgta ggtggcaagc gttgtccgga    540
attattgggc gtaaagcgcg cgcaggtggt tcttaagtc tgatgtgaaa gcccacggct    600
caaccgtgga gggtcattgg aaactgggag acttgagtgc agaagaggat agtggaattc    660
caagtgtagc ggtgaaatgc gtagagattt ggaggaacac cagtggcgaa ggcgactatc    720
tggtctgtaa ctgacactga ggcgcgaaag cgtggggagc aaacaggatt agatacctg    780
gtagtccacg ccgtaaacga tgagtgctaa gtgttagggg gtttccgccc cttagtgctg    840
cagctaacgc attaagcact ccgcctgggg agtacggtcg caagactgaa actcaaagga    900
attgacgggg gcccgcacaa gcggtggagc atgtggttta attcgaagca acgcgaagaa    960
ccttaccagg tcttgacatc ccgttgacca ctgtagagat atagtttccc cttcggggc    1020
aacggtgaca ggtggtgcat ggttgtcgtc agctcgtgtc gtgagatgtt gggttaagtc   1080
ccgcaacgag cgcaacccctt gatcttagtt gccatcattt agttgggcac tctaaggtga  1140
ctgccggtga caaaccggag gaaggtgggg atgacgtcaa atcatcatgc ccttatgac    1200
ctgggctaca cacgtgctac aatggacgat acaaacggtt gccaactcgc gagagggagc   1260
taatccgata aagtcgttct cagttcggat tgtaggctgc aactcgccta catgaagccg   1320
```

```
gaatcgctag taatcgcgga tcagcatgcc gcggtgaata cgttcccggg ccttgtacac    1380
accgcccgtc acaccacgag agtttgtaac acccgaagtc ggtgaggtaa ccttttggag    1440
ccagccgccg aaggtgggat agatgattgg ggtgaag                              1477
```

<210> SEQ ID NO 15
<211> LENGTH: 1475
<212> TYPE: DNA
<213> ORGANISM: Bacillus licheniformis IFO 12197

<400> SEQUENCE: 15

```
gacgaacgct ggcggcgtgc ctaatacatg caagtcgagc ggacagatgg gagcttgctc      60
cctgatgtca gcggcggacg ggtgagtaac acgtgggtaa cctgcctgta agactgggat     120
aactccggga aaccggggct aataccggat gcttgattga accgcatggt tcaattataa     180
aaggtggctt ttagctacca cttacagatg acccgcggc gcattagcta gttggtgagg      240
taacggctca ccaaggcaac gatgcgtagc cgacctgaga gggtgatcgg ccacactggg     300
actgagacac ggcccagact cctacgggag gcagcagtag ggaatcttcc gcaatggacg     360
aaagtctgac ggagcaacgc cgcgtgagtg atgaaggttt tcggatcgta aaactctgtt     420
gttagggaag aacaagtacc gttcgaatag ggcggtacct tgacggtacc taaccagaaa    480
gccacggcta actacgtgcc agcagccgcg gtaatacgta ggtggcaagc gttgtccgga     540
attattgggc gtaaagcgcg cgcaggcggt ttcttaagtc tgatgtgaaa gcccccggct    600
caaccgggga gggtcattgg aaactgggga acttgagtgc agaagaggag agtggaattc     660
cacgtgtagc ggtgaaatgc gtagagatgt ggaggaacac cagtggcgaa ggcgactctc    720
tggtctgtaa ctgacgctga ggcgcgaaag cgtggggagc gaacaggatt agataccctg     780
gtagtccacg ccgtaaacga tgagtgctaa gtgttagagg gtttccgccc tttagtgctg    840
cagcaaacgc attaagcact ccgcctgggg agtacggtcg caagactgaa actcaaagga     900
attgacgggg gcccgcacaa gcggtggagc atgtggttta attcgaagca acgcgaagaa    960
ccttaccagg tcttgacatc ctctgacaac cctagagata gggcttcccc ttcgggggca    1020
gagtgacagg tggtgcatgg ttgtcgtcag ctcgtgtcgt gagatgttgg gttaagtccc    1080
gcaacgagcg caaccttga tcttagttgc cagcattcag ttgggcactc taaggtgact    1140
gccggtgaca aaccggagga aggtggggat gacgtcaaat catcatgccc cttatgacct    1200
gggctacaca cgtgctacaa tgggcagaac aaagggcagc gaagccgcga ggctaagcca    1260
atcccacaaa tctgttctca gttcggatcg cagtctgcaa ctcgactgcg tgaagctgga    1320
atcgctagta atcgcggatc agcatgccgc ggtgaatacg ttcccgggcc ttgtacacac    1380
cgcccgtcac accacgagag tttgtaacac ccgaagtcgg tgaggtaacc ttttggagcc    1440
agccgccgaa ggtgggacag atgattgggg tgaag                                1475
```

<210> SEQ ID NO 16
<211> LENGTH: 1475
<212> TYPE: DNA
<213> ORGANISM: Bacillus subtilis 168 NBRC11470
<220> FEATURE:
<221> NAME/KEY: misc_feature
<222> LOCATION: (437)..(437)
<223> OTHER INFORMATION: n is a, c, g, or t

<400> SEQUENCE: 16

```
gacgaacgct ggcggcgtgc ctaatacatg caagtcgagc ggacagatgg gagcttgctc      60
```

```
cctgatgtta gcggcggacg ggtgagtaac acgtgggtaa cctgcctgta agactgggat    120
aactccggga aaccggggct aataccggat ggttgtttga accgcatggt tcaaacataa    180
aaggtggctt cggctaccac ttacagatgg acccgcggcg cattagctag ttggtgaggt    240
aacggctcac caaggcaacg atgcgtagcc gacctgagag ggtgatcggc cacactggga    300
ctgagacacg gcccagactc ctacgggagg cagcagtagg gaatcttccg caatggacga    360
aagtctgacg gagcaacgcc gcgtgagtga tgaaggtttt cggatcgtaa agctctgttg    420
ttagggaaga acaagtnccg ttcgaatagg gcggtacctt gacggtacct aaccagaaag    480
ccacggctaa ctacgtgcca gcagccgcgg taatacgtag gtggcaagcg ttgtccggaa    540
ttattgggcg taaagggctc gcaggcggtt tcttaagtct gatgtgaaag ccccggctc    600 aaccggggag ggtcattgga aactgggaa cttgagtgca gaagaggaga gtggaattcc    660
acgtgtagcg gtgaaatgcg tagagatgtg gaggaacacc agtggcgaag gcgactctct    720
ggtctgtaac tgacgctgag gagcgaaagc gtggggagcg aacaggatta gataccctgg    780
tagtccacgc cgtaaacgat gagtgctaag tgttaggggg tttccgcccc ttagtgctgc    840
agctaacgca ttaagcactc cgcctgggga gtacggtcgc aagactgaaa ctcaaaggaa    900
ttgacggggg cccgcacaag cggtggagca tgtggtttaa ttcgaagcaa cgcgaagaac    960
cttaccaggt cttgacatcc tctgacaatc ctagagatag gacgtcccct tcgggggcag   1020
agtgacaggt ggtgcatggt tgtcgtcagc tcgtgtcgtg agatgttggg ttaagtcccg   1080
caacgagcgc aaccccttgat cttagttgcc agcattcagt tgggcactct aaggtgactg   1140
ccggtgacaa accggaggaa ggtggggatg acgtcaaatc atcatgcccc ttatgacctg   1200
ggctacacac gtgctacaat ggacagaaca aagggcagcg aaaccgcgag gttaagccaa   1260
tcccacaaat ctgttctcag ttcggatcgc agtctgcaac tcgactgcgt gaagctggaa   1320
tcgctagtaa tcgcggatca gcatgccgcg gtgaatacgt tcccgggcct tgtacacacc   1380
gcccgtcaca ccacgagagt ttgtaacacc cgaagtcggt gaggtaacct tttaggagcc   1440
agccgccgaa ggtgggacag atgattgggg tgaag                              1475
```

BACTERIUM DEGRADING MICROORGANISM, MICROBIAL PREPARATION, AND METHOD AND DEVICE FOR DEGRADING MICROORGANISM

REFERENCE TO SEQUENCE LISTING SUBMITTED VIA EFS-WEB

This application includes an electronically submitted sequence listing in .txt format. The .txt file contains a sequence listing entitled "2021-03-26_Sequence_Listing_0033-1682PUS1.txt" created on Mar. 19, 2021 and is 28,672 bytes in size. The sequence listing contained in this .txt file is part of the specification and is hereby incorporated by reference herein in its entirety.

TECHNICAL FIELD

The present invention relates to bacteria that have an ability to degrade microorganisms.

BACKGROUND ART

When waste water is decontaminated by an activated sludge process, removed organic matters form flocks that contain microorganisms and sludge called excess sludge is generated. Excess sludge that is discharged from waste water treatment plants accounts for as much as 20% of the industrial wastes, and it is thus considered effective to reduce a volume of such excess sludges to reduce a volume of the industrial wastes. Excess sludge is generally dewatered, dried, and then incineration treated (NPL 1: Fiscal year of Heisei 27, Report on current status of industrial waste treatment, Results of Heisei 25 (Digest edition), NPL 2: YAMAMOTO Masayuki, "Combustion Technology of the Sewage", Journal of the Combustion Society of Japan, Combustion Society of Japan, 2011, Vol. 53, 164, p91-96).

However, incineration treatment of excess sludge generates greenhouse gasses, and thus such a treatment was not necessarily a treatment method with little impact on the environment.

CITATION LIST

Non Patent Literature

NPL 1: "Fiscal year of Heisei 27, Report on current status of industrial waste treatment, Results of Heisei 25 (Digest edition)," [online], March, Heisei 28, Minister's Secretariat, Ministry of the Environment Waste Management and Recycling Department, [searched on August 31, Heisei 30]

NPL 2: YAMAMOTO Masayuki, "Combustion Technology of the Sewage", Journal of the Combustion Society of Japan, Combustion Society of Japan, 2011, Vol. 53, 164, p91-96).

SUMMARY OF INVENTION

Technical Problem

In recent years, the society as a whole is having an increasing awareness of the global environment, and there has been a demand for a method of reducing a volume of excess sludge with even lesser impact imposed on the environment, that is, a method for degrading microorganisms composing excess sludge.

The present invention has an object to provide bacteria capable of degrading microorganisms, a microbial preparation, a method and a device for degrading microorganisms.

Solution to Problem

That is, the present invention relates to [1] to [17] given below.

[1] A bacterium having a 16S rRNA gene comprising a nucleotide sequence having 98.2% or more identity to the nucleotide sequence represented by SEQ ID NO: 1, and having an ability to degrade a target microorganism (hereinafter, also referred to as "the bacteria according to the present invention").

[2] The bacterium according to [1], having a 16S rRNA gene comprising a nucleotide sequence having 98.5% or more identity to the nucleotide sequence represented by SEQ ID NO: 1.

[3] The bacterium according to [1], having a 16S rRNA gene comprising a nucleotide sequence having 99.0% or more identity to the nucleotide sequence represented by SEQ ID NO: 1.

[4] The bacterium according to [1], having a 16S rRNA gene comprising a nucleotide sequence having 99.5% or more identity to the nucleotide sequence represented by SEQ ID NO: 1.

[5] The bacterium according to [1], having a 16S rRNA gene comprising the nucleotide sequence represented by SEQ ID NO: 1.

[6] The bacterium according to any of [1] to [5], wherein the target microorganism is a target bacterium.

[7] The bacterium according to any of [1] to [6], wherein the target microorganism is a target killed bacterium.

[8] A bacterium deposited under Accession number NITE BP-02779.

[9] A microbial preparation for degrading a target microorganism, comprising a bacterium (a1): (hereinafter, also referred to as "the microbial preparation according to the present invention")

(a1): A bacterium having a 16S rRNA gene comprising a nucleotide sequence having 90% or more identity to the nucleotide sequence represented by SEQ ID NO: 1, and having an ability to degrade a target microorganism.

[10] The microbial preparation for degrading a target microorganism according to [9], wherein the bacterium (a1) has a 16S rRNA gene comprising a nucleotide sequence having 92% or more identity to the nucleotide sequence represented by SEQ ID NO: 1.

[11] The microbial preparation for degrading a target microorganism according to [9], wherein the bacterium (a1) has a 16S rRNA gene comprising a nucleotide sequence having 95% or more identity to the nucleotide sequence represented by SEQ ID NO: 1.

[12] The microbial preparation for degrading a target microorganism according to [9], wherein the bacterium (a1) has a 16S rRNA gene comprising the nucleotide sequence represented by SEQ ID NO: 1.

[13] The microbial preparation for degrading a target microorganism according to [9], wherein the bacterium (a1) is a bacterium deposited under Accession number NITE BP-02779.

[14] The microbial preparation for degrading a target microorganism according to any of [9] to [13], further comprising a bacterium (a2):

bacterium (a2): a bacterium different from bacterium (a1), wherein the percentage of the bacteria (a1) based on the total number of the bacteria (a1) and the bacteria (a2) is 0.1% or more and 100% or less.

[15] A microbial preparation for degrading a target microorganism, comprising a culture of a bacterium (a1):

(a1): a bacterium having a 16S rRNA gene comprising a nucleotide sequence having 90% or more identity to the nucleotide sequence represented by SEQ ID NO: 1, and having an ability to degrade a target microorganism.

[16] A method for degrading a target microorganism, comprising allowing the bacterium according to any of [1] to [8] or the microbial preparation for degrading a target microorganism according to any of [9] to [15] to act on a target microorganism (hereinafter, also referred to as "the degradation method according to the present invention").

[17] A device for degrading a target microorganism, wherein the bacterium according to any of [1] to [8] or the microbial preparation for degrading a target microorganism according to any of [9] to [15] is used (hereinafter, also referred to as "the degradation device according to the present invention").

Advantageous Effects of Invention

According to the present invention, bacteria capable of degrading microorganisms, a microbial preparation, and a method and a device for degrading microorganisms can be provided.

BRIEF DESCRIPTION OF DRAWING

FIG. 1 is a chart showing a dry weight of excess sludge after addition of *Tumebacillus* sp. (NITE BP-02779) in Experiment 7.

DESCRIPTION OF EMBODIMENTS

Hereinafter, embodiments to carry out the present invention are described in detail (hereinafter, referred to as "the present embodiment"). The present invention is not limited to the following embodiments.

Descriptions of Common Terms

In the present description, the "microorganism" is a microscopic organism whose structure is unidentifiable with the naked eye and is the organisms that exclude large multicellular organisms. The "target microorganisms" are microorganisms that are degraded by the bacteria or the microbial preparation according to the present invention. Examples of such microorganisms include bacteria and fungi, and of which bacteria are preferable, with bacteria composing excess sludge being more preferable. The target microorganism can be a viable bacterium or a killed bacterium.

The "target bacteria" refers to bacteria that are to be target microorganisms and can be viable bacteria or killed bacteria, or can include viable bacteria and killed bacteria. The viable bacterium refers to a live bacterium such as a bacterium in which the metabolism occurs. The "target killed bacteria" refers to killed bacteria in the target bacteria such as a bacterium in which the metabolism does not occur. A viable bacterium and a killed bacterium can be identified by using a stain such as propidium iodide (PI). The target bacteria are preferably killed bacteria from a viewpoint of the degradation efficiency by bacteria. About 50% of the microorganisms in excess sludge is killed bacteria. Target killed bacteria can also be obtained by, for example, heating, autoclaving, UV irradiating, formalin-treating, or acid treating the target bacteria. The target killed bacteria can also be crushed bacteria.

Examples of the target microorganisms include gram-positive bacteria such as bacteria of the genus *Micrococcus*, bacteria of the genus *Bacillus*, bacteria of the genus *Staphylococcus*, bacteria of the genus *Paenibacillus*, and bacteria of the genus *Lactobacillus*, and gram-negative bacteria such as bacteria of the genus *Escherichia*, and bacteria of the genus *Acetobacter*.

In the present description, the "ability to degrade target microorganisms" refers to the ability to metabolize target microorganisms and convert biomolecules, a part or a whole, that compose the target microorganisms to different molecules. Examples of the biomolecule include sugars, proteins, nucleic acids, and lipids.

(Bacteria According to the Present Invention)

The bacteria according to the present invention has a 16S rRNA gene comprising a nucleotide sequence having 98.2% or more identity to or homology with the nucleotide sequence represented by SEQ ID NO: 1, and has an ability to degrade target microorganisms. In the present invention, the 16S rRNA gene is preferably an endogenous 16S rRNA gene that is originally present in bacteria. A 16S rRNA in which a mutation has been artificially induced can be accepted. Examples of the bacteria having a 16S rRNA gene comprising a nucleotide sequence having 98.2% or more identity to the nucleotide sequence represented by SEQ ID NO: 1 include bacteria of the genus *Tumebacillus*.

An embodiment of the bacteria according to the present invention include bacteria having a 16S rRNA gene comprising the nucleotide sequence represented by SEQ ID NO: 1, and having an ability to degrade target microorganisms.

Examples of the representative strain of bacteria having a 16S rRNA gene comprising the nucleotide sequence represented by SEQ ID NO: 1 include the strain deposited based on Budapest Treaty as *Tumebacillus* sp. (Accession number NITE BP-02779, original deposit date: Sep. 11, 2018) to the Patent Microorganisms Depositary of the National Institute of Technology and Evaluation (NPMD, address: #122, 2-5-8 Kazusakamatari, Kisarazu-shi, Chiba 292-0818). Mycological characteristics of such a strain will be shown in Tables 1 to 4 to be described later.

The bacteria according to the present invention, when compared with the nucleotide sequence represented by SEQ ID NO: 1, can have a 16S rRNA gene comprising a nucleotide sequence having 98.5% or more identity thereto or homology therewith, can have a 16S rRNA gene comprising a nucleotide sequence having 98.8% or more identity thereto or homology therewith, can have a 16S rRNA gene comprising a nucleotide sequence having 99.0% or more identity thereto or homology therewith, can have a 16S rRNA gene comprising a nucleotide sequence having 99.3% or more identity thereto or homology therewith, can have a 16S rRNA gene comprising a nucleotide sequence having 99.5% or more identity thereto or homology therewith, and can have a 16S rRNA gene comprising a nucleotide sequence having 99.8% or more identity thereto or homology therewith. The bacteria according to the present invention can be the bacteria deposited under Accession number NITE BP-02779.

Further, the bacteria according to the present invention, when compared with the nucleotide sequence represented by SEQ ID NO: 1, can have a 16S rRNA gene comprising a nucleotide sequence in which one or several bases are substituted, deleted or added. One or several bases can be, for example, 1 to 25 bases, preferably 1 to 10 bases, and more preferably 1 to 5 bases. The above mutation is a mutation by which the expression and functions of the 16S rRNA are not lost.

The bacteria according to the present invention can have a 16S rRNA gene comprising a continuous sequence of about 15 bases or more, preferably about 18 to about 500 bases, more preferably about 18 to about 200 bases, and further preferably about 18 to about 50 bases, that are included in the nucleotide sequence represented by SEQ ID NO: 1, or a nucleotide sequence hybridizable to a complementary sequence thereof under stringent conditions. The stringent conditions refer to conditions under which a non-specific hybrid is not formed and examples include a condition under which one or more washings are carried out at 60° C. with 1×SSC in 0.1% SDS, and preferably at 68° C. with 0.1×SSC in 0.1% SDS.

The ability to degrade target microorganisms of the bacteria according to the present invention varies depending on reaction conditions (kind and concentration of target microorganisms, and composition, temperature, pH, number of bacteria of a reaction solution).

For example, the representative strain of the bacteria according to the present invention *Tumebacillus* sp. (NITE BP-02779) and killed bacteria of the genus *Micrococcus* were prepared respectively to have a turbidity (OD660) of 0.2 and mixed in a volume ratio of 1:100 and reacted under a temperature condition of 20 to 35° C. at a pH condition of 6.5 to 8.0 to reduce the turbidity of one day later by about 50%, whereby the bacteria of the genus *Micrococcus* can be degraded.

The bacteria according to the present invention can be specified by the nucleotide sequence analysis of a 16S rRNA gene and the measurement of ability to degrade target microorganisms of a microorganism of interest. Specifically, when a microorganism of interest has a 16S rRNA gene comprising a nucleotide sequence having 98.2% or more homology with the nucleotide sequence represented by SEQ ID NO: 1 and has the ability to degrade target microorganisms, such a microorganism of interest can be specified as the bacterium according to the present invention.

The nucleotide sequence analysis of a 16S rRNA gene can be carried out, for example, by the following method. First, using a known method, the genetic DNA is extracted from a microorganism of interest to amplify a 16S rRNA gene. The method for amplifying a 16S rRNA gene is not particularly limited and includes a PCR method that uses universal primers typically used by a person skilled in the art. The amplified product obtained by the PCR method is purified as needed and subjected to a DNA sequencer or the like to determine a nucleotide sequence. The obtained nucleotide sequence is compared with the sequence represented by SEQ ID NO: 1.

Examples of the method for investigating the presence of ability to degrade target microorganisms include a method in which a microorganism of interest and target microorganisms are reacted for a certain time in suitable medium or a buffer solution and then the degradation of the target microorganism in the medium or buffer solution is investigated. The method for investigating the degradation is not particularly limited and examples include a method of measuring a turbidity of target microorganisms, a method of detecting target microorganisms using an SLP reagent, a method of detecting the DNA of target microorganisms by PCR, a method of measuring a dry bacterial cell weight of target microorganisms, and a method of detecting degraded products derived from target microorganisms using high performance liquid chromatography (HPLC); mass spectrometry (MS); thin layer chromatography (TLC); nuclear magnetic resonance (NMR); or gas chromatography (GC).

In the case of investigating the degradation of target microorganisms in terms of the turbidity, the presence of ability to degrade target microorganisms indicates a more significantly reduced turbidity after the reaction than a turbidity before the reaction, and the turbidity after the reaction is, for example 80% or less, preferably 50% or less, and more preferably 30% or less, of a turbidity before the reaction. In the case of investigating the degradation of target microorganisms in terms of the dry bacterial cell weight, the presence of ability to degrade target microorganisms indicates a more significantly reduced dry bacterial cell weight after the reaction than that of before the reaction, and the dry bacterial cell weight after the reaction is, for example, 95% or less, and preferably 90% or less, of that of before the reaction.

The results of these nucleotide sequence analysis and measurement of ability to degrade target microorganisms enable the conclusion of whether or not a microorganism of interest is the bacterium according to the present invention.

(Microbial Preparation According to the Present Invention)

The microbial preparation according to the present invention comprises the following bacteria (a1).

<Bacteria (a1)>

Bacteria (a1) are bacteria having a 16S rRNA gene comprising a nucleotide sequence having 90% or more identity when compared with the nucleotide sequence represented by SEQ ID NO: 1, and having the ability to degrade target microorganisms. Examples of such bacteria include bacteria of the genus *Tumebacillus*.

Bacteria (a1), when compared with the nucleotide sequence represented by SEQ ID NO: 1, can have a 16S rRNA gene comprising a nucleotide sequence having 92% or more identity thereto or homology therewith, can have a 16S rRNA gene comprising a nucleotide sequence having 95% or more identity thereto or homology therewith, can have a 16S rRNA gene comprising a nucleotide sequence having 98% or more identity thereto or homology therewith, can have a 16S rRNA gene comprising a nucleotide sequence having 99% or more identity thereto or homology therewith, can have a 16S rRNA gene comprising a nucleotide sequence having 99.5% or more identity thereto or homology therewith, and can have a 16S rRNA gene comprising a nucleotide sequence having 99.9% or more identity thereto or homology therewith. Bacteria (a1) can be the bacteria deposited under Accession number NITE BP-02779.

Further, bacteria (a1) can have a 16S rRNA gene comprising a nucleotide sequence in which one or several bases are substituted, deleted or added when compared with the nucleotide sequence represented by SEQ ID NO: 1. One or several bases can be, for example, 1 to 135 bases, preferably 1 to 100 bases, more preferably 1 to 50 bases, further preferably 1 to 25 bases, and particularly preferably 1 to 5 bases. The above mutation is a mutation by which the expression and functions of the 16S rRNA are not lost.

Bacteria (a1) can have a 16S rRNA gene comprising a continuous sequence of about 15 bases or more, preferably about 18 to about 500 bases, more preferably about 18 to about 200 bases, and further preferably about 18 to about 50 bases, that are included in the nucleotide sequence represented by SEQ ID NO: 1, or a nucleotide sequence hybridizable to a complementary sequence thereof under stringent conditions.

The nucleotide sequence analysis of a 16S rRNA gene and the measurement of ability to degrade target microorganisms of bacteria (a1) can be carried out in the same manner as for the bacteria according to the present invention described above.

Bacteria (a1) are, due to a good ability to degrade target microorganisms, preferably the bacteria according to the present invention or any of the bacteria selected from the following group A, with the bacteria according to the present invention being more preferable. Bacteria (a1) can be a single bacterium or multiple species of bacteria.

Group A: *Tumebacillus* algifaecis, *Tumebacillus* avium, *Tumebacillus* flagellates, *Tumebacillus* ginsengisoli, *Tumebacillus* lipolyticus, *Tumebacillus* luteolus, *Tumebacillus* permanentifrigoris, *Tumebacillus* soli The microbial preparation can contain a culture of bacteria (a1). The culture of bacteria (a1) refers to, for example, liquid medium containing secretion, metabolite of bacteria (a1). Specifically, the culture includes a culture of bacteria (a1) grown under controlled conditions in predetermined liquid medium or in liquid medium containing a carbon source and a nitrogen source. The microbial preparation for degrading a target microorganism containing the culture of target bacteria (a1) can contain viable bacteria of bacteria (a1). The culture of bacteria (a1) can be a culture supernatant obtained by culturing bacteria (a1). The culture supernatant can be obtained by removing bacteria (a1) from liquid medium in which bacteria (a1) is cultured by centrifugation, filtration operation or the like. Further, the culture can contain fragments of bacteria (a1). Fragments of bacteria (a1) can also be obtained by subjecting bacteria (a1) to, for example, ultrasonic disintegration, bead grinding, or chemical dissolution treatment.

The microbial preparation can contain, other than bacteria (a1), bacteria (a2), additives (b), and a carrier (c) as needed. Specific examples of the microbial preparation can include microbial preparations containing bacteria (a1), bacteria (a2), additives (b), and carrier (c).

<Bacteria (a2)>

Bacteria (a2) are bacteria different from bacteria (a1). Bacteria (a2) are not particularly limited as long as bacteria do not deprive of the ability to degrade target microorganisms of bacteria (a1), and can be a single bacterium or multiple species of bacteria.

Bacteria (a2) can be specified by the nucleotide sequence analysis of a 16S rRNA gene and the measurement of ability to degrade target microorganisms of a microorganism of interest. Specifically, when a microorganism of interest has a 16S rRNA gene comprising a nucleotide sequence having less than 90% identity to the nucleotide sequence represented by SEQ ID NO: 1 or does not have the ability to degrade microorganisms, such a microorganism of interest can be specified as bacteria (a2).

The nucleotide sequence analysis of a 16S rRNA gene and the measurement of ability to degrade target microorganisms of a microorganism of interest can be carried out in the same manner as for the bacteria according to the present invention described above.

The percentage of bacteria (a1) based on the total number of bacteria (a1) and bacteria (a2) can be 0.1% or more and 100% or less, 1% or more and 100% or less, 10% or more and 100% or less, 50% or more and 100% or less, 75% or more and 100% or less, 90% or more and 100% or less, 95% or more and 100% or less, and less than 100%. These percentages can provide efficient degradation of target microorganisms.

The percentage of bacteria (a1) based on the total number of bacteria (a1) and bacteria (a2) is the percentage of bacteria (a1) in the all bacteria contained in the microbial preparation. Examples of the method for calculating the percentage of bacteria (a1) based on the total number of bacteria (a1) and bacteria (a2) include methods that calculate by clone library method, next-generation sequencer analysis, and quantitative PCR.

In the method for calculating a percentage of bacteria present by the clone library method and next-generation sequencer analysis, specifically the genomic DNAs are extracted from bacteria (a1) and bacteria (a2) contained in a microbial preparation to obtain multiple nucleotide sequences of 16S rRNA genes (hereinafter, the number of multiple nucleotide sequences obtained is described as a lead number), and the obtained nucleotide sequences are determined respectively which of bacteria (a1) or bacteria (a2) they are derived from. Then, the percentage of the number of nucleotide sequences derived from bacteria (a1) based on the lead number is calculated to define the percentage of bacteria (a1) based on the total number of bacteria (a1) and bacteria (a2).

The next-generation sequencer used for the next-generation sequencer analysis is not particularly limited as long as it can determine a nucleotide sequence by using a DNA fragment as a template and detecting a fluorescence intensity when each base is resynthesized. Examples of the next-generation sequencer include MiSeq, HiSeq 2500 (manufactured by Illumina, Inc.), 5500xl SOLiD™, Ion Proton™, Ion PGM™ (manufactured by Thermo Fisher Scientific), and GS FLX+ (manufactured by Roche Diagnostics).

In the method for calculating a percentage of bacteria present by quantitative PCR, specifically the number of 16S rRNA gene copies of bacteria (a1) and the number of 16S rRNA gene copies of bacteria (a1) and bacteria (a2) contained in a microbial preparation of interest are respectively calculated. Then, the percentage of the number of 16S rRNA gene copies of bacteria (a1) based on the number of 16S rRNA gene copies of bacteria (a1) and bacteria (a2) is calculated to define the percentage of bacteria (a1) based on the total number of bacteria (a1) and bacteria (a2). Such a method can specify that the microbial preparation of interest is the microbial preparation according to the present invention.

The real-time PCR system used for quantitative PCR is not particularly limited as long as it is equipped with a thermal cycler capable of amplifying DNA by PCR and a spectrofluoro-photometer for detecting the amplified products. Examples of the real-time PCR system include StepOnePlus (manufactured by Applied Biosystems), Thermal Cycler Dice Real Time System (manufactured by Takara Bio Inc.), and LightCycler 96 System (manufactured by Roche Diagnostics).

Examples of the master mix used for quantitative PCR include Fast SYBR Green Master Mix, Power SYBR Green Master Mix, SYBR Select Master Mix, and PowerUp SYBR Green Master Mix (manufactured by Thermo Fisher Scientific).

<Additives (b)>

Examples of additives (b) include surfactants, dispersants, adjuvants, and protectants. The kind and concentration of the additives (b) can be suitably determined by conditions under which bacteria (a1) are not killed, or the ability to degrade target microorganisms of such bacteria is not lost.

<Carrier (c)>

Examples of carrier (c) include inorganic fine particle carriers. The inorganic fine particle carrier can be metals and inorganic salts or oxides thereof, can be those containing carbon, or can be those chemically classified as an inorganic matter. The carrier can also be a pure matter with an organic carbon content of less than about 1% or a mixture.

A central particle size of the inorganic fine particle carrier is preferably 1 µm to 100 µm, more preferably 4 µm to 75 km, and further preferably 13 µm to 25 km. When a central particle size is within such a range, bacteria (a1) is likely to be supported on the inorganic fine particle carrier. The central particle size herein refers to a median size (D50) in the volume-based particle size distribution by laser diffraction light scattering method.

The specific gravity of inorganic fine particle carrier is not particularly limited and preferably 1.2 to 3.5.

The inorganic fine particle carrier can be aggregated using various flocculants as needed for the purpose of improving a yield at the initial stage of culture.

Examples of the flocculant include nonionic, cationic, and anionic polymeric flocculants.

Examples of the method for producing the microbial preparation include a method in which bacteria (a1) and an inorganic fine particle carrier are mixed to support bacteria (a1) on the inorganic fine particle carrier and cultured to collect a microbial preparation to be obtained.

For the culture method, any of batch, semi-batch, fed-batch, or continuous mode can be used. For the culture method, for example, a continuous culture mode can be used in which, as described in Japanese Patent Laying-Open No. 9-187272, a concentration of a compound of interest supplied to a vessel in which microorganisms are cultured (hereinafter referred to as a reactor) is logarithmically increased as culture time proceeds from a viewpoint of efficiently preparing microorganisms having slow growth and low bacterial yield.

In the present invention, the formulation technique of microorganisms is not particularly limited as long as the ability to degrade target microorganisms of bacteria (a1) is not lost, and a known formulation technique can be utilized. The form of microbial preparation can be liquid or solid (including an encapsulated form, an agar-like form, a powder form and the like) and can be a frozen form or a freeze-dried form thereof. When the microbial preparation is liquid, a bacterial suspension in which bacteria are suspended in medium, a buffer solution, physiological saline or the like can also be accepted. When the microbial preparation is a solid or freeze-dried form, for example, cultured bacteria are concentrated, then suitably dried or freeze-dried to prepare a solid or freeze-dried form. During this procedure, an excipient or the like can be added.

(Degradation Method According to the Present Invention)

The degradation method according to the present invention comprises allowing the bacteria according to the present invention or the microbial preparation according to the present invention to act on target microorganisms.

The allowing the bacteria according to the present invention or the microbial preparation according to the present invention to act on target microorganisms refers to, for example, allowing the bacteria according to the present invention or the microbial preparation according to the present invention, or a solution in which these are suspended, to contact target microorganisms. When the bacteria according to the present invention or the microbial preparation according to the present invention is allowed to act on target microorganisms, the target microorganisms are degraded.

The step of allowing the bacteria according to the present invention or the microbial preparation according to the present invention to act on target microorganisms is not particularly limited as long as it is conditions under which the bacteria or bacteria (a1) according to the present invention are not killed, or the ability to degrade target microorganisms of such bacteria is not lost. Such a step can be under the condition of a temperature of 20 to 35° C. or can be under the condition of a temperature of 25 to 30° C. The step can also be under the pH condition of 6.5 to 8.0 or can be under condition of 7.0 to 7.5.

Example of the bacteria used in the degradation method according to the present invention include *Tumebacillus* sp. (Accession number NITE BP-02779).

The load of bacteria according to the present invention or the microbial preparation according to the present invention that is allowed to act on target microorganisms can be suitably set in consideration of the concentration of target microorganisms, the volume of reaction system and the like.

In the degradation method according to the present invention, the method for confirming the degradation of target microorganisms is not particularly limited and the confirmation is carried out by a method typically used by a person skilled in the art. Examples of such a confirmation method include the method for measuring the ability to degrade target microorganisms described above.

As described above, the bacteria according to the present invention and the microbial preparation according to the present invention have the ability to degrade target microorganisms and thus are useful for treating excess sludge containing target microorganisms. Further, the bacteria or the microbial preparation according to the present invention degrades target microorganisms when allowed to act thereon, and thus the degradation method according to the present invention is useful for treating excess sludge containing target microorganisms.

(Degradation Device According to the Present Invention)

The device is not particularly limited as long as it can reduce excess sludge using the bacteria according to the present invention or the microbial preparation according to the present invention and, for example, sludge treatment device and waste water treatment device from which excess sludge is generated can be used as the degradation device. Further, the bacteria according to the present invention or the microbial preparation according to the present invention is added to the existing sludge treatment device or waste water treatment device in which excess sludge is present to use as a device for degrading target microorganisms.

EXAMPLES

Experiment 1. Search for Microorganisms Having the Ability to Degrade Target Microorganisms (Method)

Using medium containing bacteria of the genus *Micrococcus* as a carbon source, a microorganism flora present in the environment (water) was cultured to subject the microorganisms that degrade the bacteria of the genus *Micrococcus* to enrichment culture. Then, several strains that grew well were isolated from the enriched microorganism flora.

(Results)

Each of the isolated strains was investigated for the ability to degrade the bacteria of the genus *Micrococcus*, and one strain demonstrated the ability to degrade the bacteria of the genus *Micrococcus*. Hereinafter, the strain that demonstrated the ability to degrade the bacteria of the genus *Micrococcus* may be described as "strain A".

Experiment 2. Analysis of Nucleotide Sequence of 16S rRNA Gene of the Strain Having the Ability to Degrade the Bacteria of the Genus *Micrococcus*

(Materials)
R2A Medium: Medium obtained by dissolving R2A Broth, DAIGO (manufactured by Nihon Pharmaceutical Co., Ltd.) in a proportion of 3.2 g in 1000 mL of ultrapure water and being autoclaved
Forward primer for cloning (27f: SEQ ID NO: 2)
Reverse primer for cloning (1492r: SEQ ID NO: 3)
Primers for sequence analysis (339F: SEQ ID NO: 4, 536R: SEQ ID NO: 5, 907F: SEQ ID NO: 6)
(Method)
DNA was extracted from strain A using Easy Extract for DNA (manufactured by AMR Incorporated) and used as a template DNA for amplifying the 16S rRNA gene by PCR.

PCR was carried out under the following conditions. 25.0 μL of 2×PCR buffer for KOD FX (manufactured by TOYOBO CO., LTD.), 10.0 μL of dNTP mix (2 mM), 1.5 μL of forward primer for cloning and reverse primer for cloning (each 10 pmol/μL), 0.58 μL of the template DNA, 10.4 μL of sterilized water, and 1.0 μL of DNA polymerase (KOD FX, 1 U/μL, manufactured by TOYOBO CO., LTD.) were added to a microtube and mixed. The microtube was subjected to a PCR system to carry out the amplification reaction of the template DNA. The reaction was carried out at (1) 94° C. for 2 minutes, (2) 98° C. for 10 seconds, (3) 50° C. for 30 seconds, and (4) 68° C. for 1.5 minutes, and 35 cycles were repeated to carry out steps (2) to (4). The amplified product after PCR was purified.

The purified PCR amplified product in an amount equivalent 150 ng, 0.32 μL of the primers for sequence analysis (10 μM) and 8.0 μL of BigDye Terminator v3.1 (manufactured by Applied Biosystems) were mixed, and sterilized ultrapure water was added thereto to prepare a reaction solution having a fluid volume of 20.0 μL. This reaction solution was subjected to PCR system to carry out the amplification reaction. The reaction was carried out at (1) 96° C. for 1 minutes, (2) 96° C. for 10 seconds, (3) 50° C. for 5 seconds, (4) 60° C. for 4 minutes, and 25 cycles were repeated to carry out steps (2) to (4). The obtained reaction solution was purified, the purified solution was subjected to the DNA sequence analysis (3730xll DNA Analyzer) to determine the nucleotide sequence of 16S rRNA gene of the template DNA extracted from strain A.
(Results)
The obtained nucleotide sequence was subjected to homology analysis with the International Nucleotide Sequence Databases (DDBJ/ENA(EMBL)/GenBank). This sequence had 98.1% identity with the nucleotide sequence of 16S rRNA gene of *Tumebacillus permanentifrigoris* Eurl_9.5 among the type strains. However, a microorganism having the 16S rRNA gene completely identical to the obtained nucleotide sequence was not present.

The obtained nucleotide sequence of the 16S rRNA gene is shown in SEQ ID NO: 1. This suggests that the bacteria having the 16S rRNA gene having the nucleotide sequence represented by SEQ ID NO:1 has the ability to degrade microorganisms.

Experiment 3. Morphological Observation and Physiological and Biochemical Property Tests of the Bacteria of the Genus *Tumebacillus* Having the 16S rRNA Gene Having the Nucleotide Sequence Represented by SEQ ID NO: 1

(Method)
Morphological observation and physiological and biochemical property tests were carried out on strain A. These tests were carried out by morphological observation using an optical microscope, the method of BARROW et al. (Cowan and Steel's Manual for the Identification of Medical Bacteria 3rd Edition 1993, Cambridge University Press.) and API50CHB (manufactured by bioMerieux, Lyon, France). Tests results are shown in Table 1 to Table 4.
(Results)
Strain A did not glow at 10° C. but this property was not found in *Tumebacillus permanentifrigoris* Eurl_9.5, which has the highest homology with the 16S rRNA gene. For this reason, it is suggested that strain A is a new species different from the conventional *Tumebacillus*. Strain A was deposited under *Tumebacillus* sp. NITE BP-02779.

TABLE 1

| Test items | Results |
| --- | --- |
| Culture temperature (° C.) | 25 |
| Cell morphology | Rod-shaped (0.8-0.9 × 3.0-5.0 μm) |
| Gram staining | + |
| Presence or absence of spore | + |
| Motility | − |
| Colony morphology | Medium: R2A agar |
| | Culture time: 48 hr |
| | Diameter: 1-2 mm |
| | Color tone: yellow |
| | Shape: circular |
| | Elevation condition: similar to a lens (elevated in the center) |
| | Margin: undulate |
| | Surface appearance etc.: smooth |
| | Transparency: opaque |
| | Viscosity: similar to butter |
| Growth temperature test (° C.) | 37 + |
| | 45 − |
| Catalase reaction | +w |
| Oxidase reaction | − |
| Acid/gas production from glucose (Acid production/gas production) | −/− |
| O/f test (Oxidation/fermentation) | −/− |

+: positive,
−: negative,
+w: weak reaction

TABLE 2

| | Test results |
| --- | --- |
| Test items (Fermentability test) | |
| Control | − |
| Glycerol | − |
| Erythritol | − |
| D-Arabinose | − |
| L-Arabinose | − |
| Ribose | − |
| D-Xylose | − |
| L-Xylose | − |
| Adonitol | − |
| β-Methyl-D-xylose | − |
| Galactose | − |
| Glucose | − |
| Fructose | − |

TABLE 2-continued

| | Test results |
|---|---|
| Mannose | − |
| Sorbose | − |
| Rhamnose | − |
| Dulcitol | − |
| Inositol | − |
| Mannitol | − |
| Sorbitol | − |
| α-Methyl-D-mannoside | − |
| α-Methyl-D-glucoside | − |
| N-Acetylglucosamine | − |
| Amygdalin | − |
| Arbutin | − |
| Aesculin | − |
| Salicin | − |
| Cellobiose | − |
| Maltose | − |
| Lactose | − |
| Melibiose | − |
| Saccharose | − |
| Trehalose | − |
| Inulin | − |
| Melezitose | − |
| Raffinose | − |
| Starch | − |
| Glycogen | − |
| Xylitol | − |
| Gentiobiose | − |
| D-Turanose | − |
| D-Lyxose | − |
| Substrate ingredient (Fermentability test) | |
| D-Tagalose | − |
| D-Fucose | − |
| L-Fucose | − |
| D-Arabitol | − |
| L-Arabitol | − |
| Gluconate | − |
| 2-Ketogluconate | − |
| 5-Ketogluconate | − |

+: positive,
−: negative

TABLE 3

| Substrate ingredients (Biochemistry test) | Test results |
|---|---|
| β-Galactosidase | − |
| Arginine dihydrolase | − |
| Lysine decarboxylase | − |
| Ornithine decarboxylase | − |
| Citric acid usability | − |
| H$_2$S production | − |
| Urease | − |
| Tryptophan deaminase | − |
| Indole production | − |
| Acetoin production (VP) | − |
| Gelatinase | − |
| Nitrate reduction | − |

+: positive,
−: negative

TABLE 4

| Test items | Test results |
|---|---|
| Growth at 10° C. | − |
| Growth at pH 9.0 | + |
| Hydrolysis of starch | + |

+: positive,
−: negative

Experiment 4. Degradation Ability Evaluation of *Tumebacillus* sp. NITE BP-02779 on Target Bacteria (Killed Bacteria)

(Materials)
R2A Medium: Medium obtained by dissolving R2A Broth, DAIGO (manufactured by Nihon Pharmaceutical Co., Ltd.) in a proportion of 3.2 g in 1000 mL of ultrapure water and being autoclaved LB Liquid medium: Medium obtained by dissolving LB Broth, 1.1G PER TABLET (manufactured by SIGMA) in a proportion of 10 tablets in 500 mL of ultrapure water and being autoclaved 802 Medium: Medium obtained by dissolving 10 g of polypeptone, 2 g a yeast extract and 1 g of magnesium sulfate heptahydrate in ultrapure water, being adjusted to pH 7.0, then prepared to be 1000 mL and autoclaved Medium for bacteria: Medium obtained by dissolving 20 g of glucose, 5 g of polypeptone, 3 g of a yeast extract, 3 g of a meat extract, 2 g of ammonium sulfate, 1 g of monopotassium dihydrogen phosphate and 0.5 g of magnesium sulfate heptahydrate in ultrapure water, being adjusted to pH 7.0, then prepared to be 1000 mL and autoclaved Target bacterium (killed bacterium)-containing inorganic medium: Medium obtained by mixing 986 mL of a substrate solution, 3.0 mL of a solution A, 3.0 mL of a solution B, 3.0 mL of a solution C, 3.0 mL of a solution D and 1.8 mL of 1% phosphoric acid Note that the above substrate solution and solutions A to D used were as follows.

Substrate solution: Solution obtained by culturing a target bacterium shown in Table 5 under the conditions shown in the same table, being collected and washed, and mixed in such a way as to have a turbidity (OD660) of 0.2 to 986 mL of ultrapure water and autoclaved Solution A: Solution obtained by dissolving 4.35 g of dipotassium hydrogenphosphate, 1.70 g of monopotassium dihydrogen phosphate, 8.92 g of di-sodium hydrogenphosphate 12-Water and 0.34 g of ammonium chloride in ultrapure water, then being prepared to be 200 mL and autoclaved Solution B: Solution obtained by dissolving 4.50 g of magnesium sulfate heptahydrate in ultrapure water, then being prepared to be 200 mL and autoclaved Solution C: Solution obtained by dissolving 5.50 g of calcium chloride anhydrous in ultrapure water, then being prepared to be 200 mL and autoclaved Solution D: Solution obtained by dissolving 0.05 g of iron chloride hexahydrate in ultrapure water, then being prepared to be 200 mL and filter sterilized with a 0.2 μm syringe filter

TABLE 5

| Target bacteria | Medium | Culture temperature (° C.) |
|---|---|---|
| *Micrococcus* | 802 Medium | 25 |
| *Bacillus* | Medium for bacteria | 25 |
| *Staphylococcus* | R2A Medium | 30 |
| *Lactobacillus* | 802 Medium | 25 |
| *Paenibacillus* | Medium for bacteria | 25 |
| *Escherichia* | LB Medium | 37 |
| *Acetobacter* | 802 Medium | 25 |

(Method)

*Tumebacillus* sp. NITE BP-02779 was seeded in R2A medium and cultured at 25° C. for 24 hours to 48 hours.

After the completion of culture, 50 µL of the *Tumebacillus* sp. NITE BP-02779 culture solution and 5.0 mL of the target bacterium (killed bacterium)-containing inorganic medium were added to a test tube, reacted at 25° C. and 200 rpm and measured over time for the turbidity (OD660) of the test tube with an easy operation turbidity meter (easy operation OD monitor miniphoto 518R, manufacture by TAITEC Corporation). The number of days that has elapsed on which the turbidity (OD660) of the target bacterium (killed bacterium)-containing inorganic medium showed 50% of the turbidity (OD660) of negative control was calculated and the presence or absence of degradation ability was decided by the following criteria.

A: 0 Days or more and less than 2.0 days

B: 2.0 Days or more and less than 5.0 days

C: 5.0 Days or more

Note that for the negative control, the turbidity (OD660) of target bacterium (killed bacterium)-containing inorganic medium to which *Tumebacillus* sp. NITE BP-02779 was not added was used.

(Results)

The results are shown in Table 6. When *Tumebacillus* sp. NITE BP-02779 was added, decreases in the turbidity of target bacterium (killed bacterium)-containing inorganic medium were observed. Thus, *Tumebacillus* sp. NITE BP-02779 was capable of degrading the target microorganisms (target killed bacteria).

TABLE 6

| Target bacteria (killed bacteria) | Results | Cell morphology | Gram staining |
|---|---|---|---|
| Micrococcus | A (0.7 days) | Coccus | Positive |
| Bacillus | A (0.8 days) | Rod-shaped | Positive |
| Staphylococcus | A (1.9 days) | Coccus | Positive |
| Lactobacillus | A (1.9 days) | Rod-shaped | Positive |
| Paenibacillus | A (1.1 days) | Rod-shaped | Positive |
| Escherichia | A (0.6 days) | Rod-shaped | Negative |
| Acetobacter | A (0.7 days) | Rod-shaped | Negative |

Experiment 5. Degradation Ability Evaluation of *Tumebacillus* sp. NITE BP-02779 on Target Bacteria (Viable Bacteria)

(Materials)

Target bacterium (viable bacterium)-containing inorganic medium: Solution obtained by mixing 986 mL of sterilized water, 3.0 mL of solution A, 3.0 mL of solution B, 3.0 mL of solution C, 3.0 mL of solution D, 1.8 mL of 10% phosphoric acid and target bacterium (viable bacterium) Note that the same solutions as in Experiment 4 were used as solutions A to D.

Further, the target bacterium (viable bacterium) was mixed so that the turbidity (OD660) of the target bacterium (viable bacterium)-containing inorganic medium was 0.2.

(Method)

The degradation ability of *Tumebacillus* sp. NITE BP-02779 on the target bacteria (viable bacteria) was evaluated by the same method as in Experiment 4 in the exception that the target bacterium (viable bacterium)-containing inorganic medium was used.

(Results)

The results are shown in Table 7. When *Tumebacillus* sp. NITE BP-02779 was added, decreases in the turbidity of the target bacterium (viable bacterium)-containing inorganic medium were observed. Thus, *Tumebacillus* sp. NITE BP-02779 was capable of degrading the target bacteria (viable bacteria).

TABLE 7

| Target bacteria (viable bacteria) | Results | Cell morphology | Gram staining |
|---|---|---|---|
| Micrococcus | B (2.0 days) | Coccus | Positive |
| Staphylococcus | A (1.5 days) | Coccus | Positive |

Experiment 6. Degradation Ability Evaluation of *Tumebacillus* sp. NITE BP-02779 on Excess Sludge (Killed Bacteria) (1)

Excess sludge (killed bacteria)-containing inorganic medium: Medium obtained by mixing 986 mL of a substrate solution, 3.0 mL of solution A, 3.0 mL of solution B, 3.0 mL of solution C, 3.0 mL of solution D and 1.8 mL of 1% phosphoric acid Substrate solution: Solution obtained by washing the excess sludge, then mixing the sludge in such a way as to have a turbidity (OD660) of 0.2 to 986 mL of ultrapure water and being autoclaved The same solutions as in Experiment 4 were used in the exception that the above substrate solution was used.

(Method)

The degradation ability of *Tumebacillus* sp. NITE BP-02779 on the excess sludge (killed bacteria) was evaluated by the same method as in Experiment 4 in the exception that the excess sludge (killed bacteria)-containing inorganic medium was used.

(Results)

The results are shown in Table 8. When *Tumebacillus* sp. NITE BP-02779 was added, a decrease in the turbidity of excess sludge (killed bacteria) was observed. Thus, *Tumebacillus* sp. NITE BP-02779 was capable of degrading the excess sludge (killed bacteria).

[Table 8]

TABLE 8

| Target bacteria (killed bacteria) | Results | Cell morphology | Gram staining |
|---|---|---|---|
| Excess sludge | B (3.2 days) | — | — |

Experiment 7. Degradation Ability Evaluation of *Tumebacillus* sp. NITE BP-02779 on Excess Sludge (Killed Bacteria) (2)

(Materials)

The same materials as in Experiment 6 were used.

(Method)

The reaction was carried out by the same method as in Experiment 4. The quintuplicate reaction was serially carried out, and the total amount of excess sludge remained in a test tube was collected on day 4 since the reaction had started. The collected excess sludge was dried and then measured for a dry weight of the excess sludge to carry out the significance test (t-test, one-sided) between the negative control group and the *Tumebacillus* sp. NITE BP-02779 addition group.

(Result)

The result is shown in FIG. 1. A significant decrease (p<0.01) in the dry weight of excess sludge was observed in the *Tumebacillus* sp. NITE BP-02779 addition group in comparison with the negative control group. Thus, the excess sludge was reducible by the addition of *Tumebacillus* sp. NITE BP-02779.

Experiment 8. Degradation Ability Evaluation of Microbial Preparations for Degrading a Target Microorganism on the Bacteria of the Genus *Micrococcus*

(Materials)

For target bacterium-containing inorganic medium, target bacterium (killed bacterium)-containing inorganic medium that contains the bacteria of the genus *Micrococcus* used in Experiment 4 as the target bacteria was prepared. The bacteria shown in Table 9 were prepared as the bacteria to be evaluated for the presence or absence of microorganism degradation ability.

TABLE 9

*Tumebacillus* sp. NITE BP-02779
*Tumebacillus algifaecis* NBRC108765t
*Bacillus alvei* IFO 3343t
*Bacillus badius* ATCC 14574t
*Bacillus brevis* IFO 3331
*Bacillus brevis* JCM 2503t
*Bacillus cereus* JCM 2152t
*Bacillus cereus* var. *juroi* ATCC 21281
*Bacillus circulans* ATCC 13403
*Bacillus circulans* IFO 3329
*Bacillus coagulans* JCM 2257t
*Bacillus firmus* JCM 2512t
*Bacillus lentus* JCM 2511t
*Bacillus licheniformis* ATCC 14594
*Bacillus licheniformis* ATCC 27811
*Bacillus licheniformis* IFO 12195
*Bacillus licheniformis* IFO 12197
*Bacillus licheniformis* IFO 12200t
*Bacillus macerans* JCM 2500t
*Bacillus megaterium* ATCC 13639
*Bacillus megaterium* IFO 12108
*Bacillus megaterium* JCM 2506t
*Bacillus moritai* ATCC 21282
*Bacillus pabuli* IFO 13638t
*Paenibacillus polymyxa* IFO 3020
*Paenibacillus polymyxa* JCM 2507t
*Bacillus pumilus* IFO 12092t
*Bacillus sphaericus* SC1713
*Bacillus sphaericus* ATCC 14577
*Bacillus sphaericus* IFO 3341
*Bacillus sphaericus* IFO 3525
*Bacillus sphaericus* IFO 3526
*Bacillus sphaericus* IFO 3527
*Bacillus sphaericus* IFO 3528
*Bacillus subtilis* JCM 1465t
*Bacillus subtilis* 168 NBRC111470
*Bacillus subtilis* ATCC 14593
*Bacillus subtilis* IFO 03108
*Bacillus subtilis* IFO 03134
*Bacillus subtilis* IFO 13169
*Bacillus subtilis* IFO 3026
*Bacillus amyloliquefaciens* NBRC3037
*Bacillus thuringensis* ATCC 13366
*Bacillus validus* IFO 13635

(Method)

The target bacterium-containing inorganic medium and the culture solution containing the bacterium to be evaluated were mixed by the same method as in Experiment 4 to evaluate the microorganism degradation ability of the bacteria to be evaluated. The number of days that has elapsed on which the turbidity (OD660) of the target bacterium-containing inorganic medium showed 50% of the turbidity (OD660) of negative control was calculated and the presence or absence of microorganism degradation ability was decided by the following criteria.

A: 0 Days or more and less than 1.0 day
B: 1.0 Day or more and less than 4.0 days
C: 4.0 Days or more Note that for the negative control, the turbidity (OD660) of target bacterium-containing inorganic medium to which the culture solution containing the bacterium to be evaluated was not added was used.

(Results)

The results are shown in Table 10. Further, a homology search of the nucleotide sequences of 16S rRNA genes of the bacteria to be evaluated shown in Table 9 against the nucleotide sequence (SEQ ID NO: 1) of 16S rRNA gene of *Tumebacillus* sp. NITE BP-02779 was carried out and calculated identity proportions are shown in Table 10. The nucleotide sequences of 16S rRNA genes of the bacteria shown in Table 10 are shown as SEQ ID NOs: 7 to 16. These are the sequences that are listed in National Institute of Technology and Evaluation, Biological Resource Center (NBRC) online catalogue or National Center for Biotechnology Information, NCBI database catalogue.

*Tumebacillus* sp. NITE BP-02779 and *Tumebacillus algifaecis* NBRC108765t had Grade A but the *Bacillus* genus bacteria and the *Paenibacillus* genus bacteria had Grade B or Grade C. Thus, *Tumebacillus* sp. NITE BP-02779 and *Tumebacillus algifaecis* NBRC108765t had superior ability to degrade target microorganisms (target killed bacteria) to bacteria of the genus *Bacillus* and bacteria of the genus *Paenibacillus*.

The identity of the nucleotide sequence of 16S rRNA gene of *Tumebacillus* sp. NITE BP-02779 to the nucleotide sequence of 16S rRNA gene of *Tumebacillus algifaecis* NBRC108765t was 92.8%. On the other hand, the identity of the nucleotide sequence of 16S rRNA gene of *Tumebacillus* sp. NITE BP-02779 to the nucleotide sequence of 16S rRNA of the bacteria of the genus *Bacillus* or the bacteria of the genus *Paenibacillus* was less than 90%. This finding led to consider that the bacteria having 90% or more nucleotide sequence identity of 16S rRNA gene to *Tumebacillus* sp. NITE BP-02779 are superior in the ability to degrade target microorganisms. *Tumebacillus algifaecis* NBRC108765t can be obtained from NBRC, and the nucleotide sequence of 16S rRNA gene thereof is listed in GenBankdEMBL/DDBJ database under Accession No. JX110710.

TABLE 10

| Bacteria to be evaluated | Results | Sequence identity |
|---|---|---|
| *Tumebacillus* sp. NITE BP-02779 | A (0.3 days) | — |
| *Tumebacillus algifaecis* NBRC108765t | A (0.8 days) | >90% (92.8) |
| *Paenibacillus polymyxa* JCM 2507t | B (1.1 days) | <90% (85.3) |
| *Bacillus amyloliquefaciens* NBRC3037 | B (1.2 days) | <90% (86.7) |
| *Bacillus subtilis* IFO 3134 | B (2.2 days) | <90% (86.7) |
| *Bacillus subtilis* IFO 3026 | B (2.9 days) | <90% (86.7) |
| *Bacillus subtilis* IFO 13169 | B (2.9 days) | <90% (86.7) |
| *Bacillus sphaericus* IFO 3341 | B (3.3 days) | <90% (86.8) |

TABLE 10-continued

| Bacteria to be evaluated | Results | Sequence identity |
|---|---|---|
| *Bacillus sphaericus* IFO 3528 | B (3.6 days) | <90% (86.8) |
| *Bacillus licheniformis* IFO 12197 | B (3.6 days) | <90% (87.0) |
| *Bacillus subtilis* 168 NBRC111470 | C (4.2 days) | <90% (86.7) |
| Other (33 strains) | C (>4.2 days) | <90% |

Experiment 9. Target Microorganism Degradation Ability Evaluation of Microbial Preparations for Degrading a Target Microorganism Containing *Tumebacillus* Sp. NITE BP-02779 and *Escherichia coli*

(Materials)

For target microorganisms-containing inorganic medium, target bacteria (killed bacteria)-containing inorganic medium containing the bacteria of the genus *Micrococcus* as the target bacteria used in Experiment 4 was prepared. Further, for a microbial preparation for degrading a target microorganism, a microbial preparation containing *Tumebacillus* sp. NITE BP-02779 (bacteria (a1)) and *Escherichia coli* DH5α (bacteria (a2)) was prepared.

(Method)

First, *Tumebacillus* sp. NITE BP-02779 was cultured at 25° C. for 24 hours, and *Escherichia coli* DH5α was cultured at 37° C. for 24 hours.

After the culture, the *Tumebacillus* sp. NITE BP-02779 culture solution (prepared to be OD660=0.2) and the *Escherichia coli* DH5α culture solution (prepared to be OD660=0.2) were mixed in ratios shown in Table 11 to prepare microbial preparations for degrading a target microorganism. 50 μL of the prepared microbial preparation and 5.0 mL of the target bacterium-containing inorganic medium were added to a test tube, reacted at 25° C. and 200 rpm and measured for a turbidity (OD660) of the mixed solution 2 days later with an easy operation turbidity meter (easy operation OD monitor, miniphoto 518R, manufactured by TAITEC Corporation). A proportion of the turbidity (OD660) of the target bacterium-containing inorganic medium to which the microbial preparation was added to the turbidity (OD660) of the negative control was calculated as a survival rate of the target microorganism. The ability to degrade target microorganism was evaluated by the following criteria.

A: 0% or more and less than 50%
B: 50% or more and less than 70%
C: 70% or more

Note that for the negative control, the turbidity (OD660) of target bacterium-containing inorganic medium to which the microbial preparation for degrading a target microorganism was not added was used.

(Results)

The results are shown in Table 11. The microbial preparations for degrading a target microorganism containing *Tumebacillus* sp. NITE BP-02779 and *Escherichia coli* demonstrated good ability to degrade target microorganisms.

TABLE 11

| Microbial preparations | | Survival rate of target microorganisms (%) |
|---|---|---|
| Proportion of bacteria (a1) to sum of bacteria (a1) and bacteria (a2) contained in a microbial preparation T/(T + E) × 100 | 100% | A (5%) |
| | 50% | A (22%) |
| | 25% | A (28%) |
| | 13% | A (35%) |
| | 6.3% | A (39%) |
| | 3.1% | A (36%) |
| | 1.6% | A (43%) |
| | 0.78% | A (42%) |
| | 0.39% | A (45%) |
| | 0.20% | A (48%) |
| | 0% | C (124%) |
| Negative control | | C (100%) |

T: Number of *Tumebacillus* sp. NITE BP-02779
E: Number of *Escherichia coli* DH5α
Survival rate of target microorganism (%) = OD660 (microbial preparation added)/OD660 (negative control) × 100

Experiment 10. Target Microorganism Degradation Ability Evaluation of *Tumebacillus* sp. NITE BP-02779 Culture (Materials)

For a target bacterium (viable bacterium)-containing phosphoric acid buffer solution, a solution in which 10 mL of a 66 mM potassium phosphate buffer solution (pH 6.24) and 10 mg of dry bacterial cells of the bacteria of the genus *Micrococcus* (manufactured by SIGMA-ALDRICH) were mixed was used. For the microbial preparation for degrading a target microorganism, a microbial preparation containing a culture of *Tumebacillus* sp. NITE BP-02779 (bacteria (a1)) was used.

(Method)

First, *Tumebacillus* sp. NITE BP-02779 was cultured in R2A medium for a certain time.

After the culture, the culture solution was centrifuged, and the culture supernatant from which the bacterial cells were removed was collected. 100 μL of the collected culture supernatant and 100 μL of a target bacterium-containing phosphoric acid buffer solution were added to a 96-well plate and measured at ABS 450 nm over time using a microplate reader (manufactured by Molecular Device, LLC). The ability to degrade bacteria of the genus *Micrococcus* genus (UNITS/mL) was calculated and the ability to degrade target microorganisms was evaluated by the following criteria.

S: 200 (UNITS/mL) or more
A: 100 (UNITS/mL) or more and less than 200 (UNITS/mL)
B: 20 (UNITS/mL) or more and less than 100 (UNITS/mL)
C: Less than 20 (UNITS/mL)

Note that the ability to degrade bacteria of the genus *Micrococcus* (UNITS/mL) was calculated using the following expression.

Ability to degrade bacteria of the genus *Micrococcus* (UNITS/mL)={ΔABS 450 nm/min (target bacterium-containing phosphoric acid buffer solution to which culture supernatant was added)−ΔABS 450 nm/min (target bacterium-containing phosphoric acid buffer solution to which culture supernatant was not added)}/(0.001×0.1)

(Results)

The results are shown in Table 12. It was revealed that the culture supernatant of which *Tumebacillus* sp. NITE BP-02779 was cultured for a certain time had the ability to degrade target microorganisms.

TABLE 12

| Culture time (hr) | *Micrococcus* genus bacteria degradation ability |
|---|---|
| 0 | C (13 UNITS/mL) |
| 21 | A (121 UNITS/mL) |
| 28 | S (249 UNITS/mL) |
| 46 | S (250 UNITS/mL) |
| 53 | S (252 UNITS/mL) |
| 68 | A (153 UNITS/mL) |

The invention claimed is:

1. A method for degrading a target microorganism, comprising allowing a bacterium to act on a target microorganism, wherein the bacterium has a 16S rRNA gene comprising a nucleotide sequence having 98.2% or more identity to the nucleotide sequence represented by SEQ ID NO: 1, and having an ability to degrade a target microorganism, wherein the target microorganism is selected from the group consisting of *Micrococcus, Bacillus, Staphylococcus, Lactobacillus, Paenibacillus, Escherichia,* and *Acetobacter,* and wherein the bacterium is a bacterium deposited under Accession number NITE BP-02779.

2. The method for degrading a target microorganism according to claim 1, wherein the target microorganism is a target killed bacterium.

* * * * *